(12) United States Patent
Staab et al.

(10) Patent No.: US 12,390,372 B2
(45) Date of Patent: Aug. 19, 2025

(54) COMPRESSION GARMENT WITH INDICATOR

(71) Applicant: Essity Hygiene and Health Aktiebolag, Gothenburg (SE)

(72) Inventors: Peter Staab, Hamburg (DE); Sebastian Bannwarth, Buchholz in der Nordheide (DE)

(73) Assignee: ESSITY HYGIENE AND HEALTH AKTIEBOLAG, Gothenburg (SE)

( * ) Notice: Subject to any disclaimer, the term of this patent is extended or adjusted under 35 U.S.C. 154(b) by 0 days.

(21) Appl. No.: 18/851,845

(22) PCT Filed: Mar. 28, 2022

(86) PCT No.: PCT/EP2022/058169
§ 371 (c)(1),
(2) Date: Sep. 27, 2024

(87) PCT Pub. No.: WO2023/186263
PCT Pub. Date: Oct. 5, 2023

(65) Prior Publication Data
US 2025/0107941 A1   Apr. 3, 2025

(51) Int. Cl.
*A61F 13/00*     (2024.01)
*A61F 13/08*     (2006.01)
*A61H 1/00*      (2006.01)

(52) U.S. Cl.
CPC ...... *A61F 13/085* (2013.01); *A61F 13/00059* (2013.01); *A61H 1/008* (2013.01); *A61H 2201/0192* (2013.01); *A61H 2201/169* (2013.01); *A61H 2205/10* (2013.01)

(58) Field of Classification Search
None
See application file for complete search history.

(56) References Cited

U.S. PATENT DOCUMENTS

| 5,195,950 A | 3/1993 | Delannoy |
| 6,338,723 B1 | 1/2002 | Carpenter et al. |
| 8,221,340 B2 | 7/2012 | Farrow et al. |

(Continued)

FOREIGN PATENT DOCUMENTS

WO   2008006227 A1   1/2008

OTHER PUBLICATIONS

Demand for Chapter II International Preliminary Examination under Art. 31 PCT for International Application No. PCT/EP2022/058169; International Filing Date: Mar. 28, 2022; Date of Mailing: Dec. 27, 2023; 3 pages.

(Continued)

*Primary Examiner* — Kim M Lewis
(74) *Attorney, Agent, or Firm* — CANTOR COLBURN LLP

(57) ABSTRACT

A system for determining, the pressure beneath a compression garment applied around a circumference of a body part, comprises an imaging device to produce image data representing a part of the garment at a measured location and a processing device, arranged to analyse the image data. The processing device uses the data to determine the circumference of the body part at the measured location and a tension in the part of the garment and thus derives a value for the pressure based on the circumference and tension.

21 Claims, 6 Drawing Sheets

(56) References Cited

U.S. PATENT DOCUMENTS

| | | |
|---|---|---|
| 11,206,900 B2 * | 12/2021 | Maezawa ............... A43D 1/027 |
| 2019/0208850 A1 | 7/2019 | Weiler et al. |
| 2020/0249657 A1 | 8/2020 | Schaumber |

OTHER PUBLICATIONS

International Preliminary Report On Patentability for International Application No. PCT/EP2022/058169; International Filing Date: Mar. 28, 2022; Date of Mailing: Jan. 23, 2024; 13 pages.
International Search Report & Written Opinion for International Application No. PCT/EP2022/058169; International Filing Date: Mar. 28, 2022; Date of Mailing: Dec. 6, 2022; 12 pages.
Australian Application No. 2022451472; Examination Report dated Sep. 12, 2024; 3 pages.

* cited by examiner capture marker capture left edge capture right edge take image from side of leg

COMPRESSION GARMENT WITH INDICATOR

CROSS REFERENCE TO RELATED APPLICATIONS

This application is a National Stage application of PCT/EP2022/058169, filed Mar. 28, 2022, the contents of which are incorporated by reference in their entirety herein.

TECHNICAL FIELD

The present disclosure relates to compression garments of the type applied to limbs or parts of a body that require a pressure to be applied. The disclosure also relates to methods of determining the resulting pressure at a particular location.

BACKGROUND

Compression garments such as stockings and wraps are well known for various purposes such as for providing support or compression to a limb or body part. They are particularly important in cases of circulatory disorders where it may be necessary to provide a given level of pressure to the body e.g. to prevent or reduce swelling.

Treatments using compression technology may include both medical and cosmetic treatments, including and related to such conditions as deep vein thrombosis, varicose veins, lymphedema and venous insufficiency. Increasingly, athletes may make use of compression technology in the context of training or recovery. Compression aids may be passive, in the form of elasticated garments or wraps or may include active components such as pneumatic chambers for applying and adjusting the pressure.

In many cases, the effectiveness of the treatment may be dependent on the accuracy and uniformity of the pressure that is to be maintained. In the case of stockings, this may require accurate manufacture and fitting to the precise dimension of the body part. Once fitted, the degree of compression is difficult to adjust, without the use of active means.

Another form of compression garment is the wrap, which is an adjustable item that is wrapped around the limb and closed at a given position corresponding to a degree of compression. In the following reference will be given to a limb although it will be understood that this is intended to refer to any susceptible body part, including a portion of a limb, a digit or torso. In the case of a wrap, the pressure applied can be mathematically determined based on the Young-Laplace equation by the tension per unit length of the wrap divided by the local radius. The tension, in turn is determined according to the material properties of the wrap material. For linear elastic materials, this is given by Hooke's law as the elastic modulus E, multiplied by the degree of extension or stretch D. For non-linear materials the correlation between stretch and tension must be determined or approximated. An example of a wrap is given in U.S. Pat. No. 8,221,340.

Systems have been proposed that provide printed indicia to a wrap that allow the extension to be determined for a given limb diameter (or circumference). This can be used to provide an indication of pressure, either by calculation, through the use of look-up tables or by alignment of scales printed on the wrap. One such system is the Circaid system described in U.S. Pat. No. 6,338,723 B1. Other systems of printed indicators are known from U.S. Pat. No. 5,195,950 B1. In all of these existing arrangements, the unstretched circumference of the bandage or garment must be first determined in order to assess the degree of elongation of the material in use. Systems also require interpretation and extrapolation between values in order to arrive at a final estimate of the pressure. In general, once the garment is applied, a subsequent easing or increase in the pressure cannot be determined. In certain circumstances, it is important that the pressure to be applied should be constant over time. In other cases, a medical practitioner may prescribe certain pressure regimes that may vary over time or may be different from body part to body part.

It would therefore be desirable to provide a simpler and more intuitive system that can provide directly the required information to a user, being a patient, care-giver or medical professional. The system should preferably be accurate and applicable over a wide range of values and styles of garments. It should also be able to provide the actual value of pressure, which may vary over time subsequent to the initial placement of the garment.

SUMMARY

According to an aspect of the invention, there is provided a system for determining, the pressure beneath a compression garment applied around a circumference of a body part, comprising an imaging device to produce image data representing a part of the garment at a measured location and a processing device, arranged to analyse the image data to determine both the circumference of the body part at the measured location and a degree of extension in the part of the garment and to derive a value for the pressure based on the circumference and extension.

By determining the actual circumference of the body part together with the extension at the measured location, an instantaneous value for the pressure being exerted may be calculated. For this purpose, data relating to the relation between extension and force for the garment material must be made available to the processing device. This information for transforming a degree of extension into a value for tension may be provided from a memory. For materials having a constant modulus of elasticity, the value will be directly proportion to the extension. Since most materials are non-linear, look-up tables may be provided to convert the extension into a value of tension with greater accuracy. The information may be pre-defined in the system or the system may carry out calibration steps to derive the information empirically.

In the present context, determining the circumference is intended to also include derivatives of the circumference such as the diameter or radius of the body part or a part of the circumference e.g. half of the circumference. Furthermore, reference to the circumference or radius is not intended to be limiting to body parts that have a circular cross-section. In general, body parts may deviate slightly from a perfect circle and this may be taken into account or the calculation may be based on the assumption of a circular section.

Reference to the tension in the garment is also intended to refer to the hoop tension in the circumferential direction. It is not however intended to exclude that the system may also determine other values such as the tension in a longitudinal direction of the body part in a direction orthogonal to the hoop tension. Determining the tension is also intended to denote the determination of derivatives of the tension such as the elongation, strain or stretch of the material of the garment.

The system may also include one or more compression garments. Such garments may be standard compression garments as presently used or may be specially adapted to interact with the imaging device and other components of the system. In this sense, use may be made of existing attributes of such compression garments to perform visual imaging. This may include labels, edges, seams, weaves, knits, patterns, prints or other kinds of graphical information or the like. Existing image processing technology is able to derive dimensional information in more or less reliable manner from most surfaces and with the addition of machine learning techniques can achieve significant accuracy. Existing computer vision measuring applications available for most smart phones can measure the distance between two points in a more or less accurate manner. Providing additional information on the surface of the garment can considerably increase the accuracy, as can calibration of the camera or imaging device to the particular measuring procedure.

Additionally or alternatively, the garment may be provided with one or more markers especially adapted for recognition by the imaging device in order to assist in determining the circumference and/or the tension. The skilled person will be well aware of suitable markers that may be applicable, including dots, lines, patterns and geometric shapes. The theory with respect to spatial recognition of points and lines by an imaging device is well developed both in the context of surveying using triangulation and more recently in computer vision and image recognition. Three points, forming a triangle of known size are thus sufficient to locate an imaging location. It will however be understood that more information is required if the three points can move with respect to each other by stretching or extension of the material on which the points are located.

In an embodiment, the markers may comprise at least a circumferential marker and a longitudinal marker and the imaging device is arranged to interrogate the respective circumferential and longitudinal markers to determine the circumference and/or the extension. Merely as an example, the circumferential markers may give an indication of the unstretched circumference, this could be in the manner of a simple centimetre scale showing the unstretched circumference. The longitudinal markers may be used to provide an indication of the degree of stretch or extension that has been applied to the material in the circumferential direction. For a material that has a Poisson's ratio of zero between the circumferential and longitudinal directions, a centimetre mark in the longitudinal direction would remain a centimetre even after stretching has taken place in the circumferential direction. This mark can be directly compared to the change in length of the centimetre marker in circumferential direction to determine the degree of extension. It will be understood that for most compression garments, the material used may have at least a slight positive Poisson's ratio which will need to be taken into account. It may also need to be taken account that longitudinal tension can be present in the garment.

Thus, for instance, a centimetre square marked on the compression garment and aligned with the longitudinal and circumferential directions, can provide significant information when viewed by an imaging device. The following assumes no component of tension or stretching applied in the longitudinal direction. Firstly, if the image remains rectangular, it may be assumed that the imaging location is positioned normal to the surface. If this is not the case, then the shape would appear as a trapezium and appropriate correction would be required. Based on the shortest sides, the longitudinal orientation is determined and the shape is scaled to one centimetre. The longest sides then provide an indication of the degree of extension applied. If the material has a positive Poisson's ratio, this should be applied to correct the initial longitudinal dimension. Based on the known properties of the material, the tension associated with the calculated extension can be determined.

Additional information may be determined using e.g. a repeating pattern of lines or shapes. A grid pattern of e.g. 1 cm squares can allow an imaging device to fully analyse information relating to the dimensions and extension of the pressure garment.

In another embodiment, the garment may further comprise a token that is not subject to stretching and maintains a predefined dimension. Such a token could be a 1D token such as a line or thread extending in a single direction or could be a 2D token such as a shape or tab, extending in two direction. The skilled person will be well aware that such a token can be very helpful in quickly and easily calibrating an imaging device to a given scale. Thus a tab having a dimension of a square centimetre that is not subject to stretching can be viewed in relation to a similar square that has been stretched. This can be particularly useful in the case of garments that are subject to longitudinal tension as well as circumferential tension or where there is a significant Poisson's ratio. The processing device may be arranged to compare a position or dimension of the markers with the token in order to determine the circumference of the body part and/or the tension. The use of a token is particular helpful in accurately determining the degree of extension. As noted above, computer vision techniques can achieve reasonable accuracy in terms of measurement but they may need an unstretched reference value to determine the degree of extension.

In certain embodiments, the imaging device is arranged to produce image data from a plurality of viewing locations. It will be understood that a single image may be sufficient to gather significant data regarding the measured location to determine the pressure beneath the pressure garment at the measured location. The effectiveness will however depend at least partially on the presence of sufficient markers and the required accuracy and computational complexity. Taking two images of the same measured location from different viewing locations may significantly improve the result. In the present context, the term 'measured location' may be interpreted as representing a particular longitudinal section of the compression garment. A plurality of images may be taken of the same circumferential position from different locations or images of different circumferential locations may be taken i.e. moving around the garment or body part to view it from different angles. The imaging device may be associated with a positioning device e.g. using accelerometers in order to determine the position of a first viewing location with respect to the position of a second viewing location. Reference to image data is also intended to include video data.

In another embodiment, the imaging device is arranged to produce image data at a plurality of measured locations and the processing device is arranged to determine a value for the pressure at each measured location, for example to determine a pressure gradient over the body part. The imaging device and the processing device may be integrated into a single device or may be located remotely, one from the other. The processing device may also be a distributed device e.g. with certain processes taking place at one location and other processes taking place elsewhere.

In one embodiment, the imaging device and processing device may be integral with a mobile telephone or the like. The system may operate as an application running directly on the telephone or may be partially remote with communication of data over the internet or mobile network to a processing device at a remote location. Implementation as an 'app' allows users, including care givers to easily check the placement of a pressure garment in real time by simply taking an image or multiple images of the applied garment. In addition to analysing the data and determining the pressure, the app may also instruct the user in performing the measurements by guiding them to position the camera of the mobile telephone at the correct viewing locations. In the following, reference to a personal mobile device is intended to include mobile phones, tablets and other hand held multifunctional devices provided with a screen and a user interface.

The present invention also relates to a compression garment to be applied around a circumference of a body part. In this context, the term garment is intended to be given a broad interpretation to include any item that can serve the purpose of providing pressure around all or part of a body part, including socks, tights, sleeves, stockings, leggings, braces, corsets, gloves, mittens, bands, bandages and wraps. The compression garment is arranged for use with the system described above and comprises an extensible material provided with a plurality of visible markers for interrogation by a mobile imaging device in order to determine a pressure beneath the compression garment.

For certain garments it may be desirable to monitor the pressure at certain locations and times to provide feedback regarding the quality of the fit or of the progress of the treatment. The feedback may be used as input to an expert system or other form of machine learning program, either to improve the process of fitting and manufacture of the garment or in order to improve the quality and efficacy of treatment.

For garments that are adjustable, such as bands or wraps, the determination of pressure may be used to adjust the garment e.g. by tightening or loosening the garment to increase or decrease the pressure.

In one embodiment, the garment comprises at least one circumferential panel that can be wrapped around the body part and adjustably secured in a stretched condition. Such an 'open' garment, which may be designated as a wrap, is a particularly useful form of pressure garment for the treatment of lymphedema and like ailments. It can be readily applied to any body part and does not need to be accurately tailored as is the case for compression stockings and other 'closed' garments. In certain cases, the panel will be longer in the circumferential direction than in the longitudinal direction. In other cases, it may extend in the longitudinal direction to a greater extent. The panel may also be shaped e.g. have a three dimensional form to allow for variations in circumference in the longitudinal direction of the body part.

The panel may comprise first and second ends and connecting means to adjustably secure the first end in position over the second end. The skilled person will be well aware of the range of connecting means that can be applied for this purpose, including hook and loop type connectors, straps and buckles, laces, cords, poppers, buttons, adhesives, magnetic closures and the like. At least one marker can be positioned to indicate a degree of overlap of the first end with respect to the second end. The skilled person will be well aware of the possible machine readable markers that can serve this purpose, including simple dimensional scales, intersecting lines and the like. Once the local extension of the material has been determined, the degree of overlap may be used to indirectly indicate the circumference of the body part, taking into account the initial length of the panel.

In one embodiment, the garment comprises a plurality of circumferential panels connected to each other by a longitudinal spine. Such an arrangement is a common form of wrap that allows a whole or partial limb to be uniformly compressed. Each panel may have different dimensions to allow for variations in the shape of the body part in the longitudinal direction. The panels may be relatively narrow and extend on either side of the spine. In the alternative, the panels may extend to one side of the spine only. In this case, an attachment may be provided at the spine to which the first end of the respective panel is attached.

The invention also relates to a method of determining the pressure exerted by a compression garment encircling a body part, the method comprising: i. visually analysing a part of the garment to determine a local circumference of the garment, ii visually analysing the part of the garment to determine a degree of extension of the material of the garment, with respect to an unstretched condition of the material; iii based on the local circumference and the degree of extension, computing a value for the pressure. The method may be carried out using the system as described above or otherwise. As also noted above, determining the circumference of the body part is intended to include the determination of derivatives of the circumference such as the diameter or radius.

In an embodiment, visually analysing the part of the garment to determine a degree of extension of the material of the garment comprises forming an image of the garment material and comparing a structure of the garment material in a stretched condition to a previously determined structure of the garment material in the unstretched condition. Information for transforming a degree of extension into a value for tension may be provided from a memory. For materials having a constant modulus of elasticity, the value will be directly proportion to the extension. Since most materials are non-linear, look-up tables may be provided to convert the extension into a value of tension with greater accuracy.

As mentioned above, one way of visually analysing a part of the garment to determine a degree of extension of the material of the garment comprises comparing a change of dimension in the circumferential direction with a change of dimension in a longitudinal direction. This can be achieved either using markers or the underlying material structure. Knowing Poisson's ratio for the material, the differences between these two directions allows the extension to be determined.

In an alternative, visually analysing a part of the garment to determine a degree of extension of the material of the garment may comprises comparing a part of the garment in a stretched condition with a token having a fixed dimension as also further described above.

In an embodiment, visually analysing the part of the garment to determine a local circumference of the garment may comprise interrogating markers provided on a surface of the garment. These may comprise markers placed for this specific purpose or other attributes of the garment. In this context, it is noted that the method may also or alternatively determine a local circumference of the body part. Although less preferred, it would be possible to e.g. determine a circumference of the body part prior to donning the garment.

As noted above, one method of measuring an object, that is well established in the field of mobile devices is based on computer vision imaging techniques. Existing computer vision measuring apps are able to rapidly assess the distance between two points such as the edges of a body part. Nevertheless, the accuracy depends on many factors such as the definition of the image and the presence of defined elements such as markers on the item to be measured. This accuracy may also be provided to the user e.g. in the form of error margins. Moving the imaging device provides increased information and can reduce the error margin. In one embodiment, the step of visually analysing the part of the garment to determine a local circumference of the garment may be carried out until an error margin of less than a chosen value is achieved. A user of the method may be instructed to continue the measurement or visual analysis until the required error margin is achieved. The user may also be instructed to move an imaging device in an appropriate manner to improve the measurement.

In certain circumstances, the method may comprise visually analysing the garment to determine a local circumference of the garment by viewing the garment from different positions around the circumference. This may be required for body parts that are not circular in cross-section. In that case, different diameters of the body part may be measured and averaged or a complex image of the cross-section of the body part may be established from which the circumference may be determined. It will be appreciated that the Young-Laplace equation already provides for non-circular forms.

In an embodiment, the method is carried out on a garment as described above, including socks, tights, sleeves, stockings, leggings, braces, corsets, gloves, mittens, bands and wraps.

In a still further embodiment, there is disclosed a method of applying a compression garment to a body part, the method comprising initially positioning the compression garment around the body part, performing the method as described above to compute the pressure beneath the garment, comparing the computed value for pressure to a predetermined value for pressure and adjusting the compression garment based on a difference between the computed value and the predetermined value. Adjustment may comprise opening and/or releasing part of the garment such as a closure or the like or moving the garment with respect to the body part. The method may then be repeated until the desired pressure is achieved.

In another embodiment, the method may comprise determining a volume of the body part beneath the garment and monitoring a variation of the volume over time. This approach may be used to assess the effectiveness of treatment and, based on the monitored results, provide the opportunity to optimize the therapy based on calculated customized pressure suggestions.

BRIEF DESCRIPTION OF THE DRAWINGS

The features and advantages of the present disclosure will be appreciated upon reference to the following drawings of a number of exemplary embodiments, in which.

DESCRIPTION OF ILLUSTRATIVE EMBODIMENTS

Figure 1:
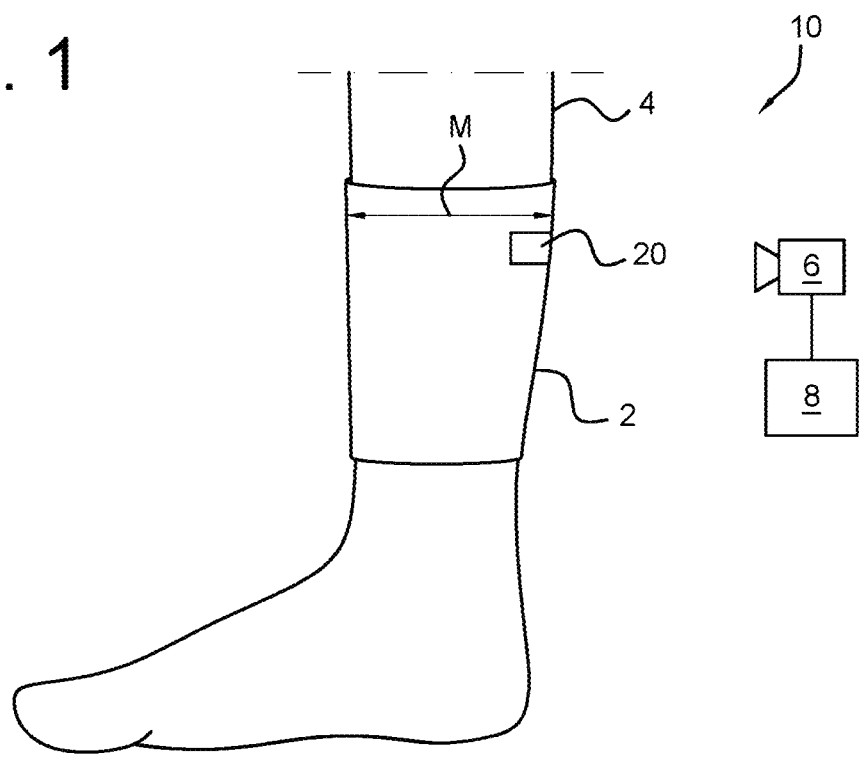
FIG. 1 shows a schematic view of a system for assessing the pressure beneath a compression garment applied around a body part.

FIG. 1 shows a schematic representation of a system 10 for assessing the pressure beneath a compression garment 2 applied around a circumference of a body part 4, comprising an imaging device 6 to produce image data representing a part of the garment at a measured location M and a processing device 8, arranged to analyse the image data to determine both the circumference of the body part at the measured location M and an extension in the part of the garment and to derive a value for the pressure based on the circumference and extension. The garment 2 includes a marker 20 located at the measured location M.

In this embodiment, the compression garment 2 is a stocking located to apply tension around a user's calf. It will be understood that the principle may be applied to other closed tubular forms and also to wraps or bandages that are applied laterally or wound around a limb or body part. The marker 20 in this embodiment has a pre-defined size and is affixed to the garment 2 at one edge such that it is not subject to the tension forces in the garment 2.

Figure 1A:
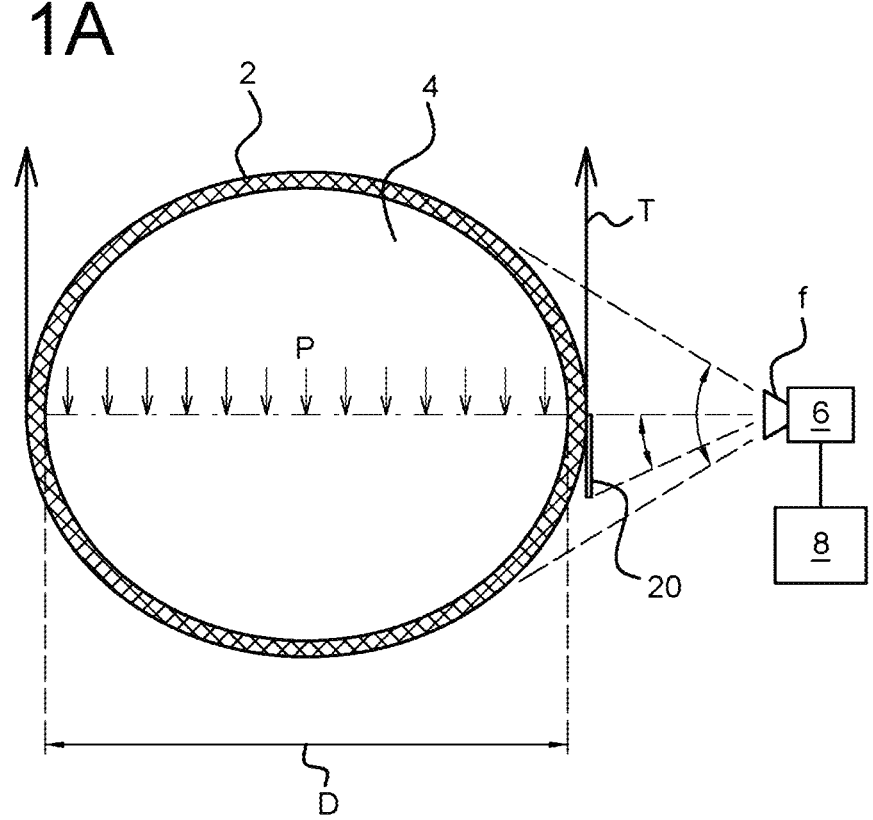
FIG. 1a shows a cross-section taken at the measured location of FIG. 1.

FIG. 1A shows a cross-sectional view through the garment 2 and body part 4 at the measured location M. As is well understood, the pressure P within a tubular body such as the garment 2 can generally be approximated as the circumferential tension T in the garment divided by the half of the diameter D. Since, in the case of a circle, the circumference of the body part 4 is related to the diameter D, measuring either the diameter directly or the circumference allows the diameter D to be determined. In the case of the tension T in the garment 2, it is necessary to measure the degree of stretch E or extension of the garment in the circumferential direction and multiply this by the modulus of elasticity of the material. For a perfectly elastic material, this may be considered a constant K whereby T=KE. The value for K may be determined in advance. For materials that are non-linear, look-up tables may provide the relation between extension E and tension T. In this case, the processing device 8 may be provided with access to a memory storing such data and may be able to interpolate between values to derive the correct value for T.

As can be seen from FIG. 1A, the marker 20 facilitates interpretation and scaling of an image formed by the imaging device 6. The processing device 8 can evaluate, based on simple geometry, the diameter at the measured location M by comparing the angle subtended by the edges of the garment 2 at the focal point f with the angle subtended by the marker.

Additionally, knowing the unstretched circumference of the garment 2 at the measured location M allows this to be compared with the measured circumference (based on 7D). It will be understood that the above assumes certain constraints, such as the body part 4 and garment 2 being circular or cylindrical at the measured location M but these are not unreasonable first order assumptions and the resulting assessment of the pressure P can be provided with the appropriate error margins. Nevertheless, it will also be understood that additional measurements may be taken from different positions and directions, whereby the overall error margins may be reduced.

Figure 2:
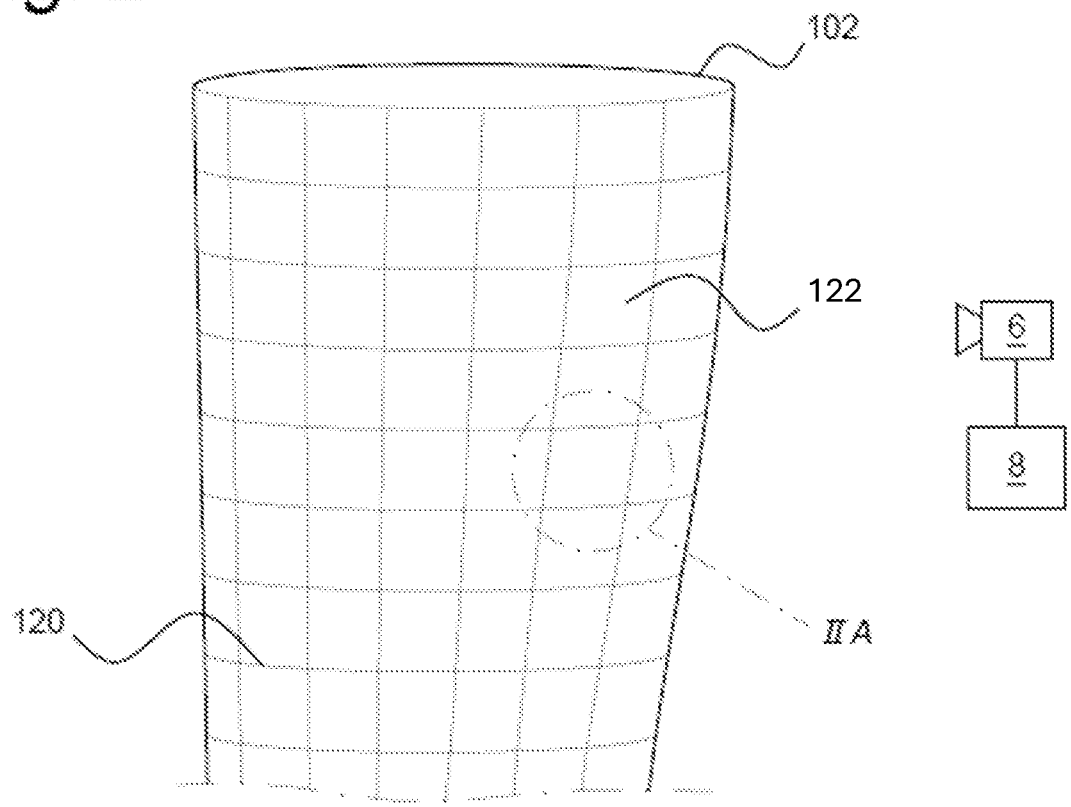
FIG. 2 shows a view of an alternative compression garment provided with a grid of markers.

FIG. 2 shows a view of an alternative compression garment in the form of a stocking 102 provided with markers in the form of a grid 120 covering the whole surface of the garment 102. The grid 120 as shown comprises 1 cm squares in the unstretched condition of the garment and is visible to the imaging device 6. The grid 120 may be part of a visible attractive pattern or print, or may even be invisible to the naked eye.

Figure 2A:
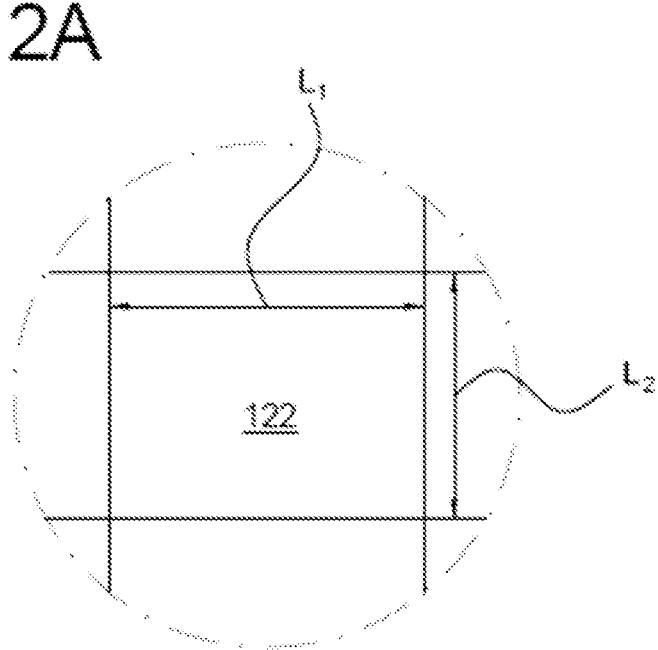
FIG. 2A shows a close up view of a portion of the garment of FIG. 2.

FIG. 2A shows a close up of part of the grid 120 of FIG. 2 illustrating a single mesh 122. The imaging device 6 perceives the mesh 122 to have dimensions L1×L2. In a first approximation, the processing device 8 may assume that Poisson's ratio for the garment material is zero. In this case, for no extension in the longitudinal direction of the garment 102, the perceived dimension L1 will still represent an actual dimension of 1 cm. The perceived dimension L2 will represent an actual dimension of L2/L1 cm. Not only does this allow the extension E to be determined but also allows the circumference and diameter to be determined. Since the grid 120 is provided over the whole stocking 102, measurements can be taken at any desired measured location M.

Figure 3:
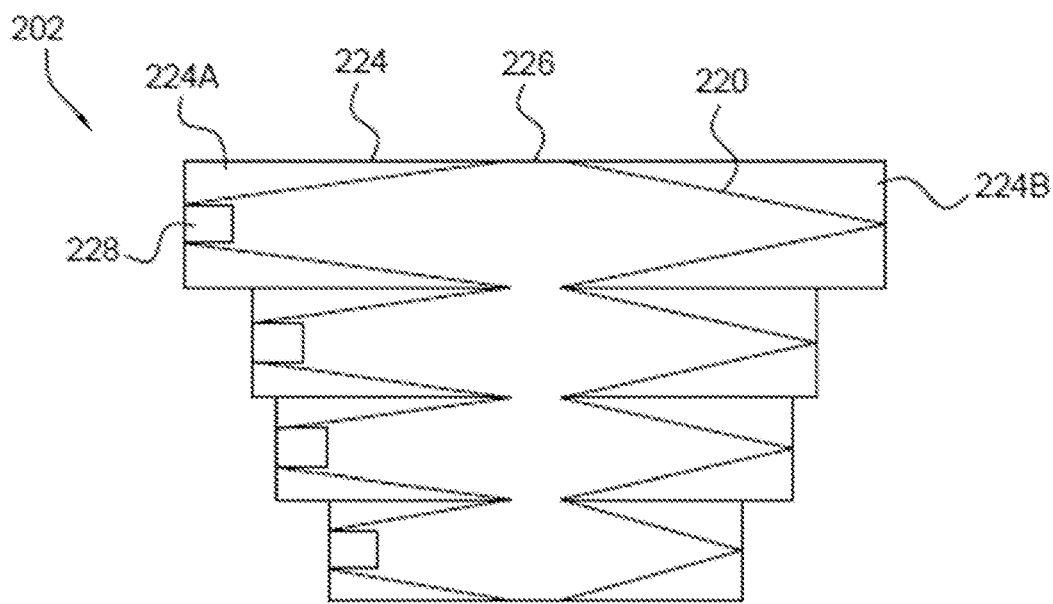
FIG. 3 shows a multi-panel compression wrap in an open configuration.

FIG. 3 shows a multi-panel compression wrap 202 of the type that is intended to be wrapped around a lower limb. The wrap 202 is in an open configuration and has a plurality of circumferential panels 224 connected to each other by a longitudinal spine 226. Each panel 224 has a first end 224A that is intended to be wrapped over a second end 224B and secured with a hook and eye fastener. A tab 228 for applying and tensioning each of the panels, is made of non-stretch material and is of a pre-defined dimension. Each panel is provided with markers in the form of tapering lines 220. The panels 224 are of different sizes to allow for the expected variations in girth of the lower limb to which it is intended to be applied.

Figure 4:
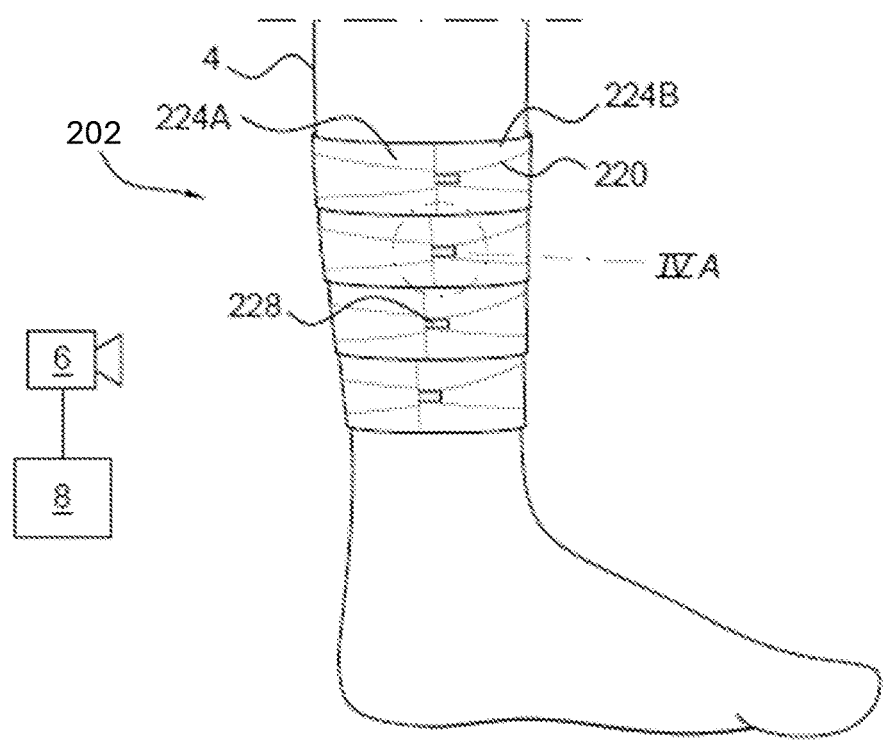
FIG. 4 shows the compression wrap of FIG. 3 applied to a body part.

FIG. 4 shows the compression wrap 202 of FIG. 3 in place around a body part 4. A characteristic of wraps is that they are adjustable and the effective unstretched circumference of each individual panel can thus vary. A user or carer will apply the wrap 202 and apply tension to the tab 228 based on personal judgement. The degree of tension applied may depend upon the time of day, the position of the limb and also the sequence in which the different panels 224 are fastened. It will be understood that the effectiveness of the therapy may be critically affected by the degree of tension and pressure applied.

According to FIG. 4, it can be seen that the first ends 224A of the panels 224 are overlapped over the respective second ends 224B. The tapered lines 220 at the first ends 224A have a width W2, which in this embodiment also corresponds to a width of the tab 228. In the wrapped condition, this end 224A partially obscures the tapering lines 220 on the second ends 224B of the panel, providing an indication of the degree of overlap. Image data received by the imaging device 6 is analysed by the processing device 8 to determine the distance between the tapering lines 220 at the point of overlap.

Figure 4A:
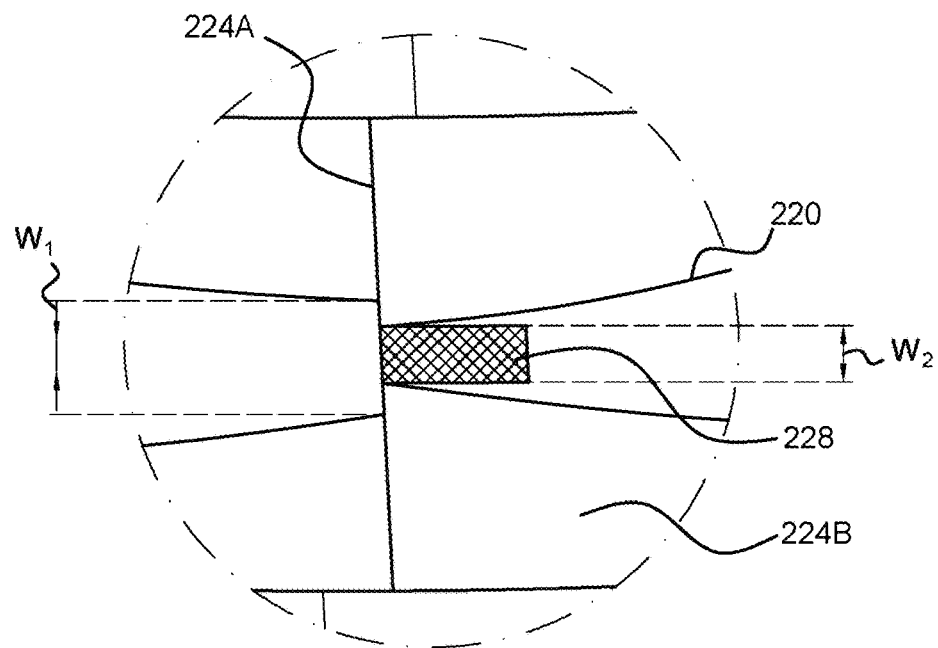
FIG. 4A shows a close up of a portion of the wrap of FIG. 3.

FIG. 4A shows a close up of a portion of the wrap 202 of FIG. 4, illustrating the width W1 between the tapered lines 220 on the second end 224B at the point of overlap. The width W2 of the lines 220 on the first end 224A is a constant. The ratio of W1/W2 allows the processing device to determine the unstretched circumference of the applied panel 224 with respect to the overall initial length. Additionally, the tab 228, provides a fixed dimension indication from which the imaging device 6 and the processing device 8 can derive the actual diameter of the body part 4 and wrap 202 at the measured location as described previously.

Figure 5:
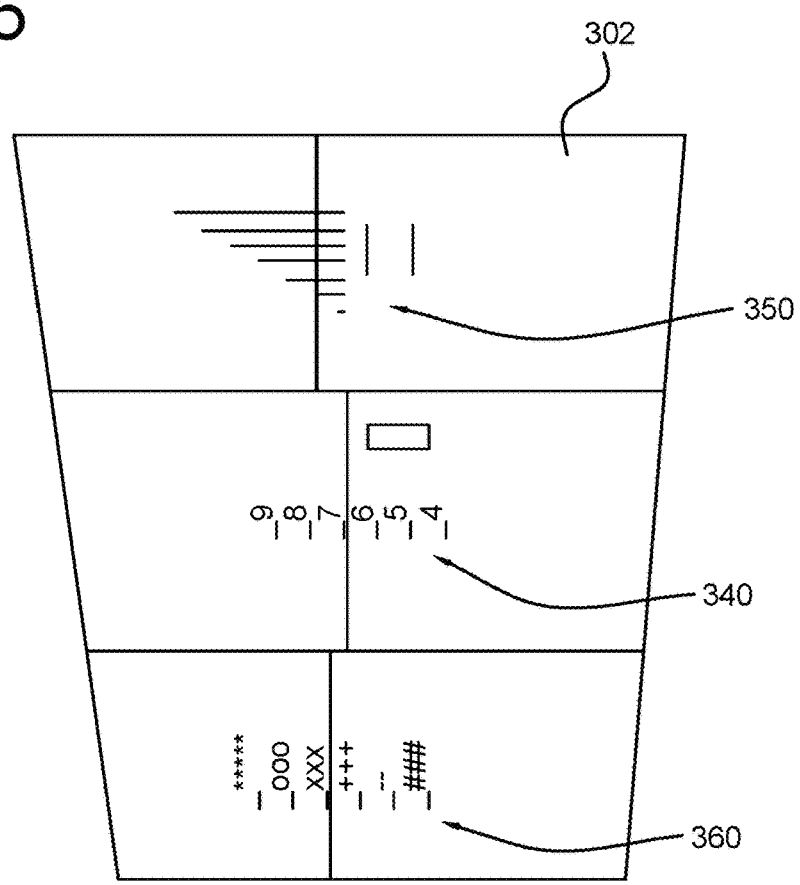
FIG. 5 shows a number of alternative markers applied to a wrap.

FIG. 5 illustrates three further alternative marking arrangements that may be applied to a wrap 302 to derive information regarding its placement. It will be well understood that many alternatives to the tapered lines of FIG. 3 can also give a representation of the unstretched circumference, including a simple centimetre scale 340 (which would no longer display actual centimetres once stretched), a series of geometric lines 350 or other markers 360. These may be combined with a grid like marker in the form of a square or similar shape, which allows the degree of extension to be determined as described in the context of FIG. 2.

FIGS. 6A to 6D show representations of a user interface 50 on a personal mobile device 52 such as a mobile phone, implementing a method of assessing the pressure beneath a compression garment as shown in FIG. 1. The method may be implemented in the form of an application downloaded and installed on the mobile device 52, whereby the imaging device 6 is provided by a camera of the mobile device 52 and processing takes place within the onboard processor.

Figure 6A:
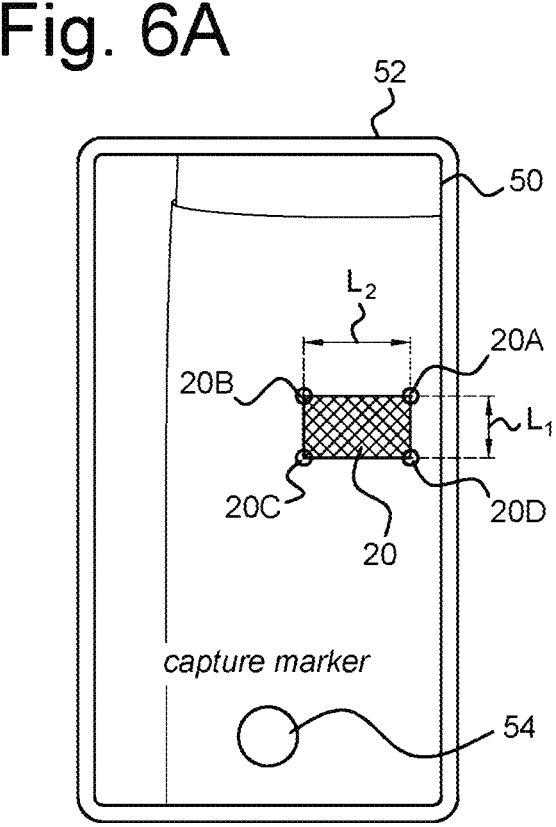
FIGS. 6A to 6D show examples of a user interface of a system performing pressure assessment of the compression garment of FIG. 1.

In FIG. 6A, the user has aimed the camera at the marker 20, which has been identified by four points aligned with the perceived corners 20A-D of the marker 20. The interface instructs a user to capture the marker 20 using a soft command button 54 on the user interface 50. The processor establishes the perceived dimensions L1, L2 of the marker 20 and compares it with the known actual dimension in order to accurately calibrate the image.

Figure 6B:
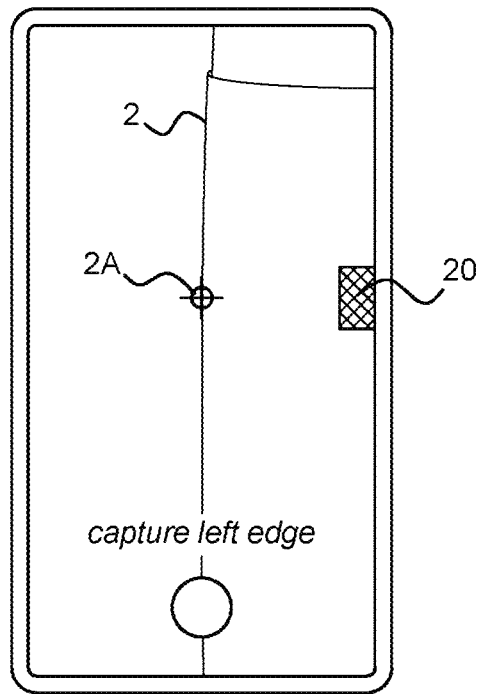

In a second step, shown in FIG. 6B, the user interface 50 prompts the user to capture the left edge 2A of the garment 2 at the same location as that of the marker 20.

Figure 6C:
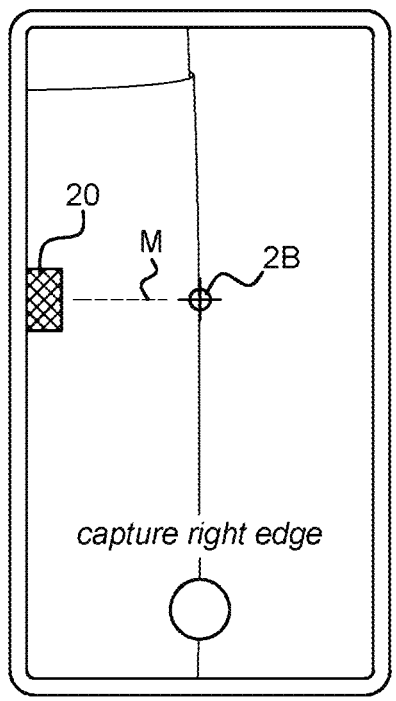
Figure 6D:
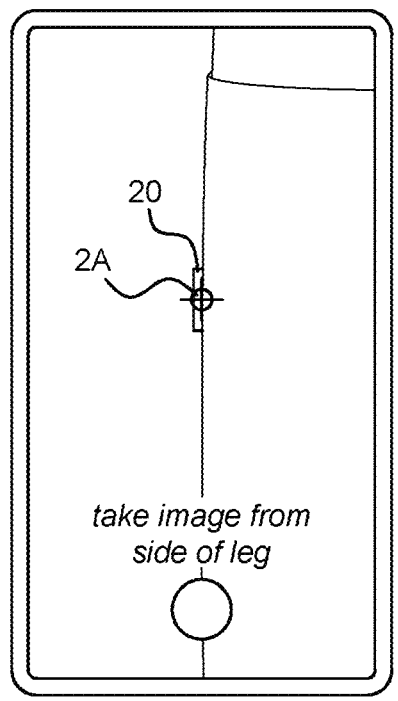

In a third step, shown in FIG. 6C the user interface 50 prompts the user to capture the right edge 2B of the garment 2. In this view, a dotted line shows the diameter of the garment 2 being measured at the measured location M, which passes through the marker 20.

In a fourth step. Shown in FIG. 6D, the user interface 50 instructs the user to move the camera to a side of the body part at a position perpendicular to the initial measurements. The edges 2A, 2B are again captured and used to compare and validate the first measurements. The user is instructed to repeat measurements until the processor 8 is satisfied that the measured co-ordinates are accurate enough for an acceptable assessment of pressure to be performed.

The illustrated embodiment of FIGS. 6A to 6D uses a single marker and provides measurement at a single measured location. It will be understood that multiple markers may be located at different positions along the compression garment corresponding to different desired or intended measured locations.

Figure 7:
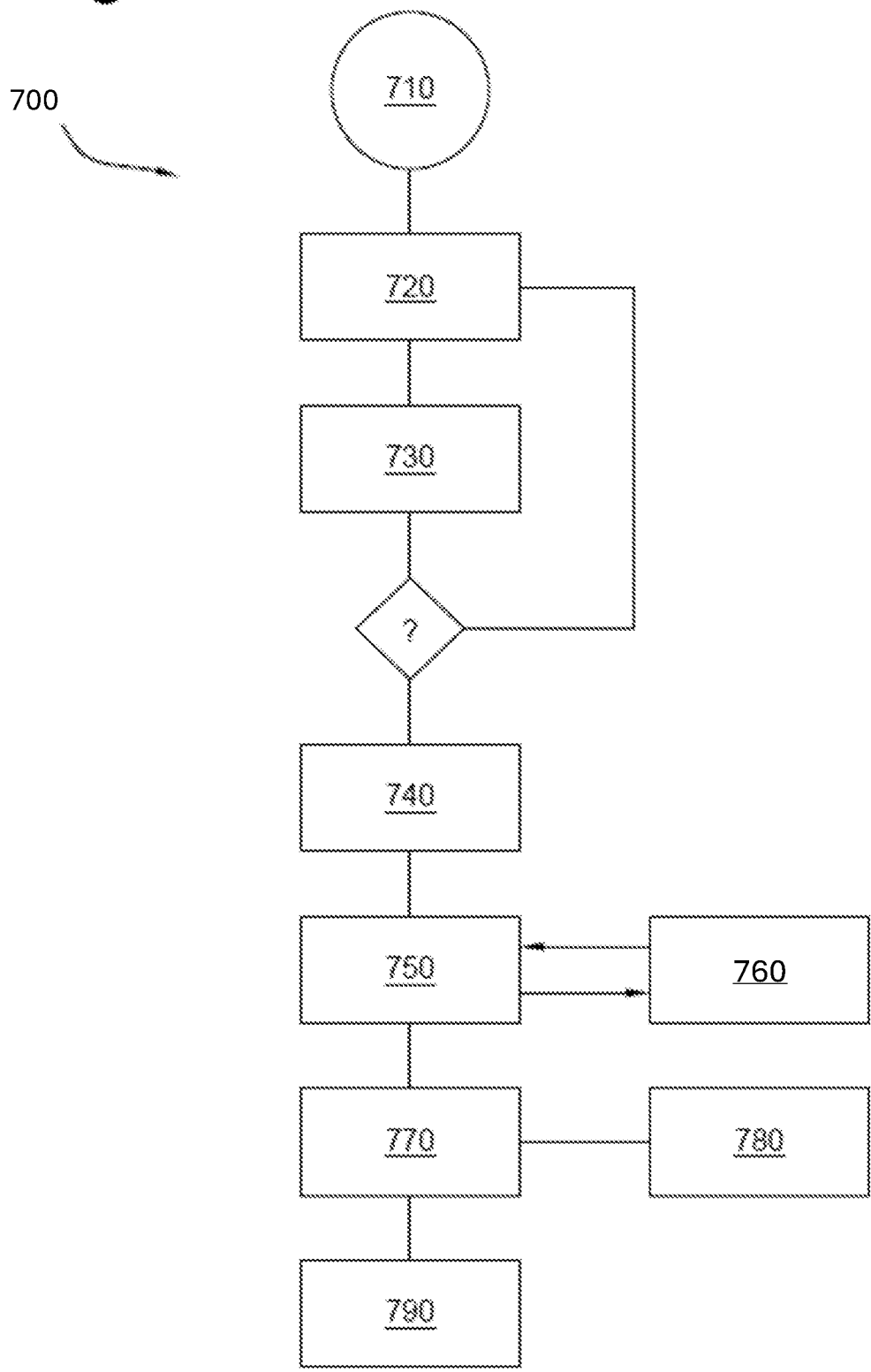
FIG. 7 shows a flow chart of a process for carrying out measurements on the wrap of FIG. 3.

Similarly, the process can be applied equally to the stocking 102 of FIG. 2 and the compression wrap 202 of FIG. 3. FIG. 7 shows a flow chart of a possible process 700 for carrying out such a measurement on the wrap of FIG. 3 using a mobile device as in FIG. 6. In step 710, the app is opened by a user in conventional manner. At step 720 the user is prompted to take an image in order to derive the required information. In particular, the app may prompt the user to take a single picture or multiple pictures from different angles. These may then be validated in terms of focus and blur at step 730 to confirm usability. If the images are unsuitable, step 720 is repeated. Appropriate computer vision software at step 740 detects information of interest from the detected markers. At 750, the processor derives an estimated value for the initial unstretched circumference of the wrap based on the markers discussed in relation to FIGS. 3 and 4. Additionally the diameter of the limb and the degree of extension can be determined from this information. Based on additional data from look-up tables or memory 760 in relation to the extension/tension characteristics of the wrap material, the processor can also derive at step 770 values for tension in the wrap and thus the pressure. This may be displayed at step 780. The user may also be notified of relevant data regarding the placement of the wrap and may be instructed to make adjustments if required at step 790.

It will be understood that the process may be carried out on placing the wrap but may also be repeated at intervals in order to determine variation over time.

Thus, the present disclosure has been described by reference to the embodiments discussed above. It will be recognized that these embodiments are susceptible to various modifications and alternative forms well known to those of skill in the art without departing from the spirit and scope of the invention as defined by the appended claims.

The invention claimed is:

1. A system for assessing a pressure beneath an elastically extensible compression garment applied around a circumference of a body part, comprising
   an imaging device to produce image data representing a part of the garment at a measured location; and
   a processing device, arranged to analyse the image data to determine both the circumference of the body part at the measured location and a degree of extension in the part of the garment and to derive a value for the pressure based on the circumference and the extension.

2. The system according to claim 1, further comprising an elastically extensible compression garment, wherein the garment is provided with one or more markers, and the system is arranged to identify the markers in order to determine the circumference and/or the extension.

3. The system according to claim 2, wherein the markers comprise a circumferential marker and a longitudinal marker and the system is arranged to interrogate the respective circumferential and longitudinal markers to determine the circumference and/or the extension.

4. The system according to claim 2, further comprising a token that is not subject to stretching and maintains a predefined dimension and the processing device is arranged to compare a position or dimension of the markers with the token in order to determine the circumference of the body part and/or the extension.

5. The system according to claim 1, wherein the imaging device is arranged to produce image data from a plurality of viewing locations and the processing device uses the image data from the plurality of viewing locations to derive the value for the extension at the measured location.

6. The system according to claim 1, wherein the imaging device is arranged to produce image data for a plurality of measured locations and the processing device is arranged to determine a value for the pressure at each measured location.

7. The system according to claim 1, wherein the imaging device and processing device are integral with a personal mobile device.

8. A compression garment to be applied around a circumference of a body part for use in a system for assessing the pressure beneath an elastically extensible compression garment applied around the circumference of the body part, the system including an imaging device to produce image data representing a part of the garment at a measured location and a processing device, arranged to analyse the image data to determine both the circumference of the body part at the measured location and a degree of extension in the part of the garment and to derive a value for the pressure based on the circumference and extension, the compression garment comprising:
   an elastically extensible material provided with a plurality of visible markers for interrogation by an imaging device to determine a pressure beneath the compression garment including at least one circumferential panel configured to be wrapped around the body part and adjustably secured in a stretched condition.

9. The garment according to claim 8, wherein the panel comprises first and second ends and connecting means to adjustably secure the first end in position over the second end.

10. The garment according to claim 9, wherein at least one marker indicates a degree of overlap of the first end with respect to the second end.

11. The garment according to claim 8, wherein at least one marker indicates a degree of extension of the extensible material with respect to a relaxed state.

12. The garment according to claim 8, comprising a plurality of circumferential panels connected to each other by a longitudinal spine.

13. A method of assessing a pressure exerted by an elastically extensible compression garment encircling a body part, the method comprising:
   i. using an imaging device, visually analysing a part of the garment to determine a local circumference of the garment at a measured location;
   ii. visually analysing the part of the garment to determine a degree of extension of the material of the garment at the measured location, with respect to an unstretched condition of the material; and
   iii. based on the local circumference and the degree of extension, computing in a processing device, a value representative of the pressure at the measured location.

14. The method according to claim 13, wherein visually analysing the part of the garment to determine a degree of extension of the material of the garment comprises forming an image of the garment material and comparing a structure of the garment material in a stretched condition to a previously determined structure of the garment material in the unstretched condition.

15. The method according to claim 13, wherein visually analysing the part of the garment to determine a degree of extension of the material of the garment comprises comparing a change of dimension in the circumferential direction with a change of dimension in a longitudinal direction.

16. The method according to claim 13, wherein visually analysing the part of the garment to determine a degree of extension of the material of the garment comprises comparing a part of the garment in a stretched condition with a token having a fixed dimension.

17. The method according to claim 13, wherein visually analysing the part of the garment to determine a local circumference of the garment comprises interrogating markers provided on a surface of the garment.

18. The method according to claim 13, wherein visually analysing the part of the garment to determine a local circumference of the garment is repeated until the processing device determines that an error margin of less than a predetermined value is achieved.

19. The method according to claim 13, wherein the garment is a garment including an elastically extensible material provided with a plurality of visible markers for interrogation by an imaging device to determine a pressure beneath the compression garment including at least one circumferential panel configured to be wrapped around the body part and adjustably secured in a stretched condition.

20. A method of applying a compression garment to a body part, the compression garment including an elastically extensible material provided with a plurality of visible markers for interrogation by an imaging device to determine a pressure beneath the compression garment including at least one circumferential panel configured to be wrapped around the body part and adjustably secured in a stretched condition, the method comprising initially positioning the compression garment around the body part, performing the method according to claim 14, comparing the computed value for pressure to a predetermined value for pressure and adjusting the position of the compression garment based on a difference between the computed value and the predetermined value.

21. A computer program product adapted to perform the method according to claim 13, when operated on a personal mobile device having a camera and user interface.

* * * * *